United States Patent [19]

Gemmer

[11] Patent Number: 4,941,770
[45] Date of Patent: Jul. 17, 1990

[54] METHOD FOR APPLYING A CONDUCTOR LAYER ON A ROAD SURFACE AND ARRANGEMENT OF A HEATING LAYER ON A ROAD SURFACE

[76] Inventor: Hans-Jürgen Gemmer, Amngelstr. 14, D-6251 Heistenbach, Fed. Rep. of Germany

[21] Appl. No.: 221,256
[22] PCT Filed: Oct. 31, 1986
[86] PCT No.: PCT/DE86/00436
 § 371 Date: Jun. 20, 1988
 § 102(e) Date: Jun. 20, 1988
[87] PCT Pub. No.: WO88/03303
 PCT Pub. Date: May 5, 1988
[51] Int. Cl.⁵ .......................... E01C 3/06; E01C 7/28; E01C 11/24
[52] U.S. Cl. ........................................ 404/72; 404/82
[58] Field of Search ................. 404/82; 427/118, 136, 427/137, 258, 286, 288, 402, 409

[56] References Cited

U.S. PATENT DOCUMENTS 2,036,373  4/1936  Taylor .
4,594,022  6/1986  Jeppson .................................. 404/82

Primary Examiner—Stephen J. Novosad
Assistant Examiner—Gay Ann Spahn
Attorney, Agent, or Firm—Toren, McGeady

[57] ABSTRACT

In order to determine traffic density it is known to embed copper wires as induction loops in grooves. The copper wires, which are protected by means of corresponding sheathings, are then covered with a silica sand layer and usually secured against floating by wood wedges. The grooves, which are cut into the road surface, are grouted with hot asphalt. Moreover, it is known to place copper layers on the road surfaces and to seal them with plastics material. But difficulties arise, particularly in the area of joints, since the latter cannot easily be bridged. The invention first provides for the arrangement of a carrier layer (13) on the road surface (11), the subsequent spraying on of the conductor layer (15), and then the sealing of the conductor layer (15) with a protective covering (14) consisting of a plastics material corresponding to the material of the carrier layer (13). If the conductor layer (15) is arranged directly on the road surface (11), connecting pieces, which can be easily sprayed over, are provided in the area of the joints, the connecting pieces being elastic within certain limits. The conductor layer (15) can also be used as a heating layer, as a guide track or as a moisture detection layer.

3 Claims, 3 Drawing Sheets

METHOD FOR APPLYING A CONDUCTOR LAYER ON A ROAD SURFACE AND ARRANGEMENT OF A HEATING LAYER ON A ROAD SURFACE

The invention is directed to a method for applying an inductive conductor layer enclosed by a protective covering on a road surface.

On the other hand, the invention is directed to an arrangement of a heating layer on a road surface according to this method according to the characteristic features in the preamble of claim 3.

In order to determine the density of traffic, for distinguishing between types of vehicles, for example, passenger cars and trucks, for measuring speed, directing, influencing and warning traffic, for controlling signal systems and for short-term counts, it is known to embed copper wires as induction loops in grooves which are particularly cut into the road surface. The copper wires are inserted at the beginning or in the middle of the loop field according to the number of windings. The copper wires generally consist of a fine-strand wire with a cross section of approximately 1.5 mm$^2$. They are provided with a silicon sheathing and are additionally protected by means of a glass fiber sheathing. The copper wires inserted in the grooves are then covered with a silica sand layer and usually secured against floating by means of wood wedges. The grooves are subsequently grouted with hot asphalt or plastics material.

In order to lower the expenditure of time for laying an inductive loop of copper wires and the costs involved, it is also known to lay copper layers on the road surfaces and to seal them with plastics material.

In such measures, the road surface is first covered with a template and then sprayed with a coupling agent in a thickness of approximately 0.1 mm. Next, a copper wire is liquified by means of metal spraying equipment and applied to the coupling agent in a layer thickness of approximately 0.3 mm. After removing the template, a protective covering of plastics material is applied and then dried.

Although only approximately ⅓ of the time required for the production of an induction loop of copper wires is required for this way of producing the inductive conductor layer, and the cost of production amounts to only approximately 30% of the cost of an induction loop, it has been shown that there is room for improvement in that road joints which are usually filled with an elastic substance cannot be bridged easily. Rather, special measures must be taken which involve additional expenditure. For example, it is necessary to use short cables as bridges which are soldered with the conductor layers on both sides of the road joint. However, such cable bridges must be embedded in cut out portions of the road and then covered. Moreover, the soldering of the cable bridges to the conductor layers require trained workers working with great care. Nevertheless, a loosening of the coupling agent previously applied to the road surface during the soldering process cannot always be avoided. But even when this work is carried out with care, the disadvantage remains that the coupling agent is soluble in water. A processing in subfreezing temperatures is therefore ruled out.

The invention has the object of providing a method ,and an arrangement which, on the one hand, enable the application of an inductive conductor layer on a road surface regardless of the prevailing temperatures, specifically also in the area of the road joints, and which, on the other hand, increase the range of application of the conductor layer while reducing production costs.

In the method according to the invention, this object is met in that after the road surface is cleaned an electrically conductive material is liquified by means of a metal spraying device and applied directly to the previously roughened road surface in a film-like manner, or is applied to a carrier layer, which is previously applied to the road surface, then roughened and which consists of a fast-setting plastics material which is resistant to temperature, abrasion and aggressive substances and remains elastic within certain limits, and is then sealed as a conductor layer with a protective covering consisting of a plastics material corresponding to the material of the carrier layer.

As a rule, a plastics material layer is first applied to a pretreated road surface as carrier layer. This carrier layer must comprise a series of characteristics in order that it may meet the proposed object. Thus, for example, it must be resistant to temperature, i.e. it must withstand high summer temperatures as well as low winter temperatures. In so doing, it must constantly retain a residual elasticity in order to participate in movements of the road without incurring damage, particularly during changes in temperature. Moreover, the carrier layer must be sufficiently resistant to abrasion with respect to the stresses caused by vehicles passing over it. Finally, it must be resistant to aggressive materials, such as salts, gasoline and oils. It is also necessary that the carrier layer set quickly in order to ensure a brief assembly time. After setting, the carrier layer is roughened and the conductor layer, particularly consisting of copper, is then applied. Subsequently, the conductor layer is sealed with a protective covering consisting of a plastics material which has the same characteristics as the plastics material of the carrier layer.

A substantial advantage of the method, according to the invention, consists in that the road joints no longer present a problem. They are simply bridged during the application of the carrier layer, so that after the protective covering is applied it forms, together with the carrier layer, a sheathing for the conductor layer which protects the latter and allows no disadvantageous effects during relative movements of the road portions located at either side of a joint.

In cases where the application of a carrier layer is not possible and the conductor layer must be applied directly to the road surface, connecting pieces, which are elastic at least to a limited degree, and which can be sprayed over when applying the conductor layer and then held in their working position by means of the protective covering, are provided in the area of the road joints. Such elastic connecting pieces participate without difficulty in the relative movements of two road portions adjacent to a road joint, so that the inductive conductor layer is never interrupted.

An advantageous embodiment form of the idea which meets the proposed object according to the subject matter of the invention is seen in a conductive layer which is applied on a cleaned road surface directly in liquid form or with the intermediary of a carrier layer, is electrically conductive and sealed with a protective covering after curing. Such arrangements can be of a diverse kind in principle. In addition to the possibilities of application already known in induction loops with copper wires, it is now also possible e.g. to use the conductor layer for the contactless control of unmanned transport vehicles in factories in an advantageous manner. The guideways can be changed relatively quickly and without much expenditure with respect to their configuration corresponding to the respective requirements.

Another interesting field of application is the automatic guiding of motor vehicles on roads.

The movements of airplanes in airports can now also be monitored with comparatively little expenditure.

Another advantageous embodiment form of the invention provides for the arrangement of a heating layer on a road surface. Heating layers are placed to an increasing extent particularly on roads with ice hazards, preferably bridge-type highway portions. The carrier layer, according to the invention, now makes it possible to compensate exactly for uneven areas of the ground. This means that the conductor layer can be applied very accurately and in a determined thickness, so that the same heat resistance can be ensured everywhere. Another advantage of using a conductor layer as a heating layer is that the supplied energy can be considerably reduced in comparison to the heating cables which were previously placed in the ground. Since the conductor layer is arranged directly at the surface, hardly any energy is lost in the warm-up phase, as is necessarily the case in known cases where the ground is first heated before the road surface is heated to the desired extent. The response time, i.e. the control dead time, during warmup is extremely short.

Finally, an advantageous embodiment form of the arrangement according to the invention is seen in the use of the conductor layer as a moisture detection layer. Since the conductor layer can be arranged over the entire width of a road, then when moisture forms at some location— as seen along the width of the road—an ice warming will be effected, for example, always in connection with a temperature sensor. Traffic safety will be greatly increased accordingly.

The connection of the conductor layer in the road can be effected in different ways, regardless of its use. However, the characteristic features of claim 6 are advantageous. In this case, a borehole which is inclined at an angle of approximately 45° can be arranged at the verge of the road (marginal strip or median strip), for example, in such a way that the borehole opens into the road surface approximately 20 cm from the verge of the road and extends 20 cm deep into the ground. A copper pipe can then be inserted into this borehole, an approximately 5×5 cm copper plate being soldered on the top of this copper plate. This copper plate can also be sprayed in without difficulty during the application of the conductor layer. A cable, which leads to a control or evaluating unit, can be soldered on at the other end of the pipe, that is, in the ground.

The invention is explained in more detail in the following with the aid of the embodiment examples shown in the drawing.

Figure 1:
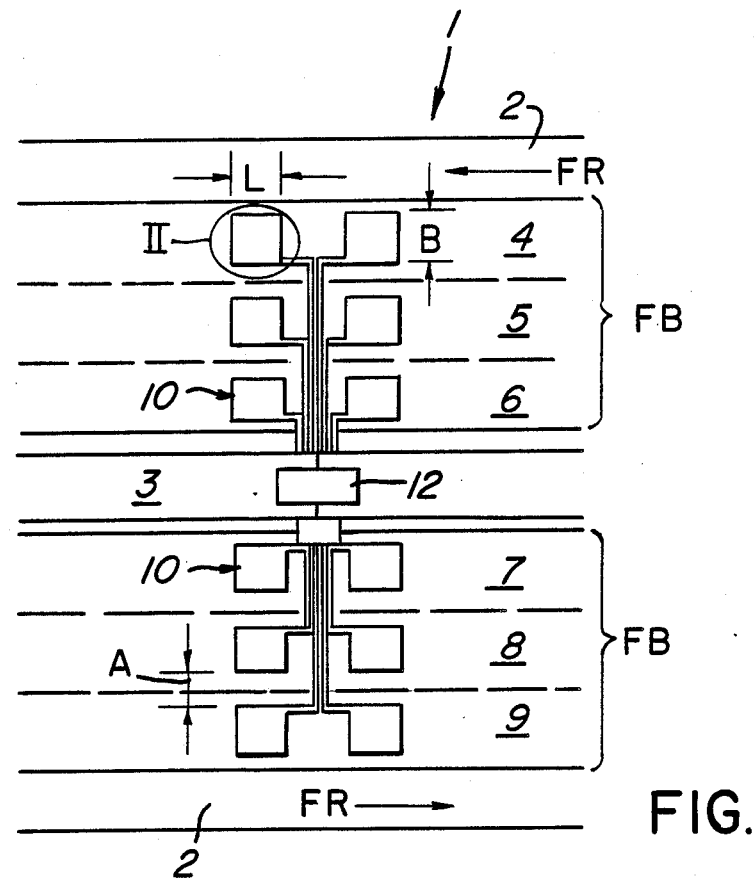
FIG. 1 shows a top view of a road portion with an arrangement for monitoring vehicle movements.

The portion of a highway 1 with two three-lane roadways FB for each driving direction FR, which is illustrated in FIG. 1, is defined at both sides of the roadways FB by a marginal strip 2. The two roadways FB are separated by means of a median strip 3. The marginal strip 2 and/or the median strip 3 can be fastened or not fastened.

Figure 2:
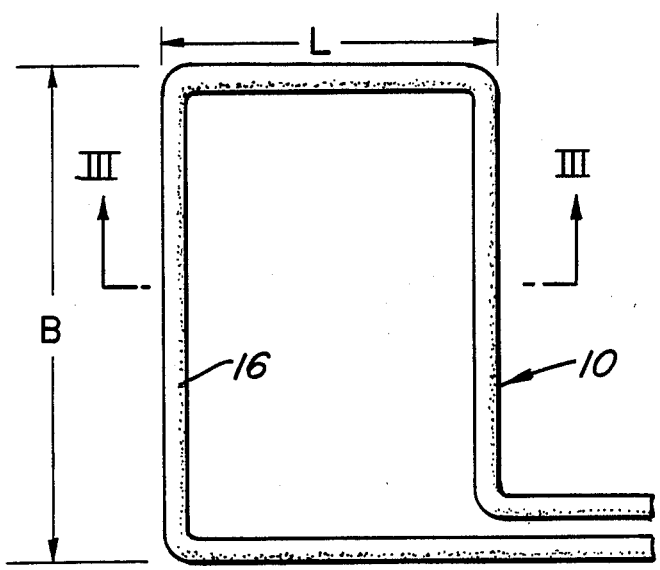
FIG. 2 shows an enlargement of section II of FIG. 1.
Figure 3:
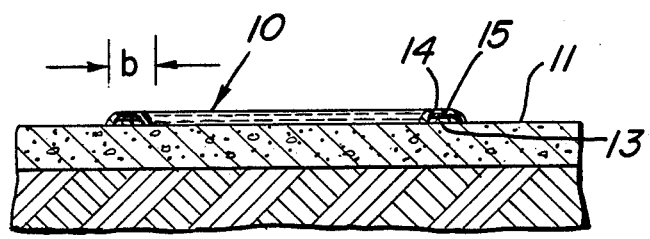
FIG. 3 shows a vertical longitudinal section through FIG. 2 along line III—III.

In order to determine or monitor the vehicle movements on the two roadways FB an induction loop 10 is placed on the road surface 11 for each lane 4–9 (FIGS. 1–3). The different induction loops 10 are guided along a point of intersection 12 provided in the median strip 3 and coupled with a control unit or evaluating unit in a manner not shown in more detail. This can be effected transversely under a roadway FB, for example, via a groove.

As can be seen in this connection when considering FIGS. 1 and 2 in combination, the length L of an induction loop 10 is approximately 2 to 3 m and the width B is approximately 1.5 to 2.5 m. The distance A between two induction loops 10 depends on the width of the lanes 4–9 or of the median strip 3.

Each induction loop 10 is composed of an electrically conductive conductor layer 15 which is applied to a cleaned road surface 11 directly in liquid form or with the intermediary of a carrier layer 13 and is sealed with a protective covering 14 after curing (FIG. 3). In order to produce such an induction loop 10, the road surface 11 is first thoroughly cleaned. A carrier layer 13, which consists of plastics material which is resistant to temperature, abrasion, aggressive substances, is fastsetting and remains elastic at least within certain limits, is then applied to the cleaned road surface 11. This carrier layer 13 can have a thickness of several hundredths of a millimeter. After the carrier layer 13 sets within a time period of approximately 5 minutes, the carrier layer 13 is roughened, a copper wire of ⅜" thickness is liquified by means of metal spraying equipment and is applied to the carrier layer 13 in a thickness of approximately 0.3 mm. The conductor layer 15 formed in this way is subsequently sealed with a plastics material which, as protective covering 14, should correspond with respect to material to the material of the carrier layer 13.

The width b of a strand 16 of an induction loop 10 is around 5 cm (FIG. 3).

Figure 4:
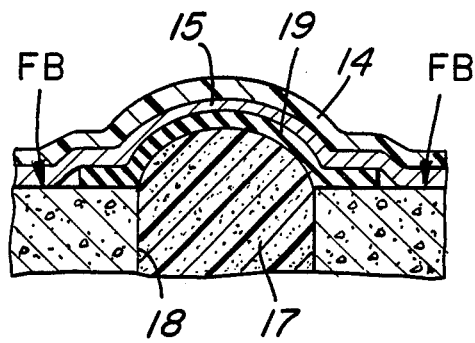
FIG. 4 shows a vertical cross section in the area of a road joint in enlarged scale.

Another embodiment form makes it possible to apply the copper conductor layer 15 directly on the road surface 11. For this purpose, the road surface 11 is first cleaned and then roughened. Connecting pieces 19, which are elastic at least within certain limits, are arranged in the area of the joints 18 of the roadway FB (FIG. 4) which are filled with asphalt 17; the connection pieces 19 can then be bridged easily when applying the conductor layer 15. The protective covering 14 can also be applied then without difficulties. The protective covering 14 then holds the connecting pieces 19 in their work position. Since the connecting pieces 19 are elastic, at least within certain limits, they participate in the relative movements of two road portions adjacent to a road joint 18 without difficulty, so that the inductive conductor layer 15 is never interrupted.

FIGS. 1 to 3 illustrate how the conductor layer 15 is intended for monitoring vehicle movements on the different lanes 4-9. However, according to the configuration of the strands 16 of an induction loop 10, the conductor layer 15 which is embedded therein can also be used to advantage for contactless control, particularly of unmanned transport vehicles in factories. The respective guide strands 16 can be changed relatively rapidly and without much expenditure with respect to their configuration, according to the respective requirements.

But it is not possible to use the induction loops 10, for example, according to FIG. 2, for controlling unmanned transport vehicles in factories. It is also conceivable to guide motor vehicles on roads automatically with such induction loops 10.

In addition, the movements of airplanes in airports can be monitored in this way with comparatively little expenditure.

Figure 5:
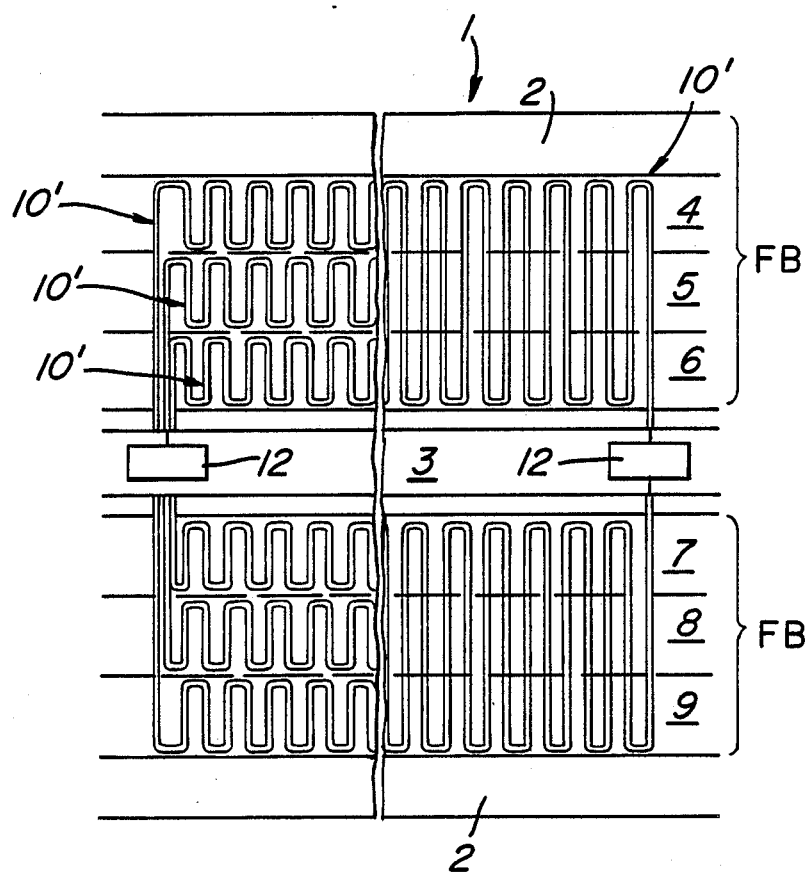
FIG. 5 shows a top view of a road portion with a conductor layer as heating layer in two different embodiment forms.

FIG. 5 shows the arrangement of an induction loop 10', which comprises a conductor layer 15, as a heating layer on a road surface 11. For this purpose, it is possible, according to the left half of FIG. 5, to provide the heating loop 10' in a winding configuration along the width of only one lane 4-9. According to the right half of the drawing, the induction loops 10' can also be arranged along the entire width of a roadway FB. Since the conductor layer 15 is embedded in the carrier layer 13, uneven portions of the ground can be exactly compensated. Consequently, the conductor layer 15 can be applied in a determined thickness and the same heating resistance is ensured everywhere (FIG. 5 in connection with FIG. 3).

Figure 6:
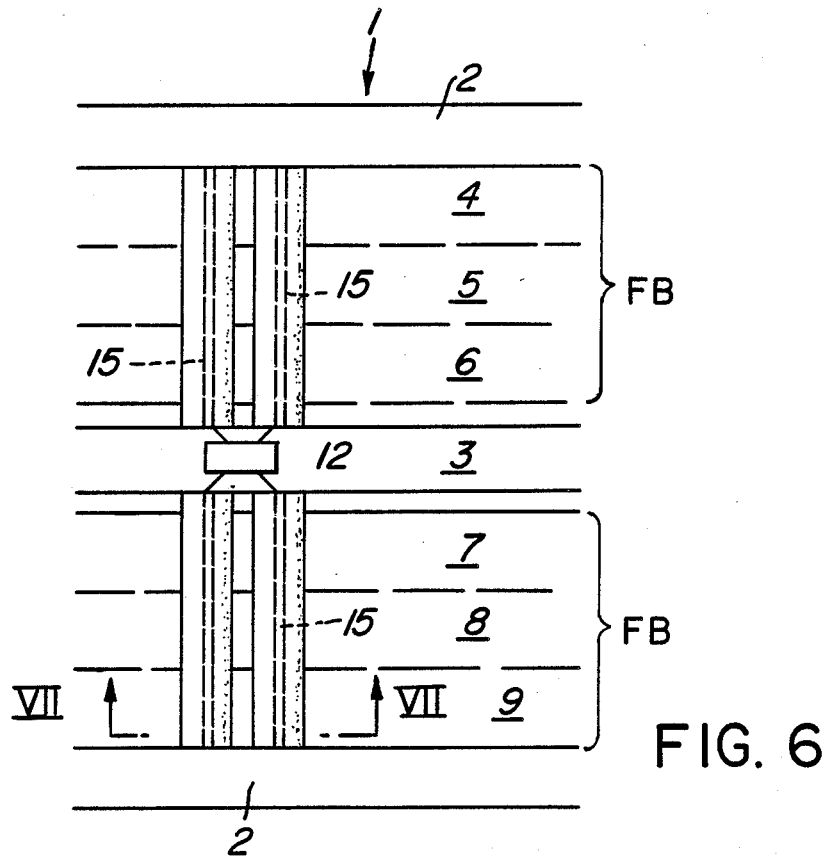
FIG. 6 shows a top view of a road portion with a conductor layer as moisture detection layer.
Figure 7:
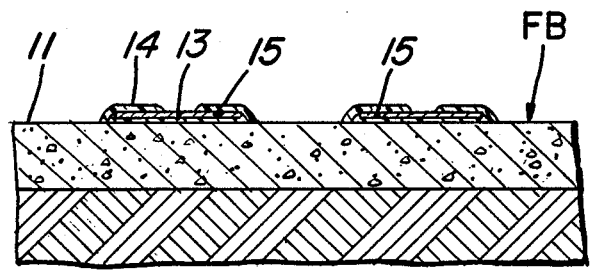
FIG. 7 shows a vertical cross section through FIG. 6 along VII—VII in enlarged scale.

FIGS. 6 and 7 show the use of the conductor layer 15 as a moisture detection layer. By means of such an arrangement, in which the conductor layers 15 are preferably arranged transversely along the entire roadway FB, it is possible, particularly during the colder seasons, to determine promptly the risk of an ice formation in connection with temperature sensors during water formation on the roadways FB, so that corresponding countermeasures may be taken promptly.

Figure 8:
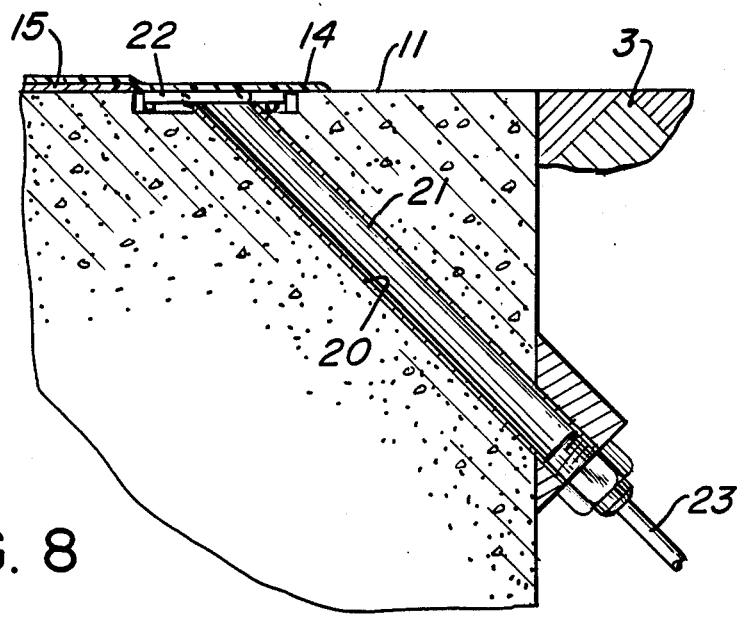
FIG. 8 shows the connection in the road of a conductor layer to a control or evaluating unit.

FIG. 8 shows the connection of a conductor layer 15 in the road, particularly in the area of the point of intersection 12. In this case, a borehole 20 is arranged at the median strip 3 at an angle of approximately 45° in such a way that it opens into the road surface 11 approximately 20 cm from the verge of the roadway and extends 20 cm deep into the ground of the median strip 3. A copper pipe 21 is inserted into the borehole 20, an approximately 5×5 cm cooper plate 22 being soldered on its upper side. The copper plate 22 can be easily sprayed in and also covered by the protective covering 14 during the application of the conductor layer 15. A cable 23, which leads to a control or evaluating unit, not shown in more detail, is fastened at the other end of the copper pipe 21, that is, in the ground 3.

I claim:

1. Method for applying an inductive conductor layer on a road surface, the conductor layer being enclosed by a protective covering, the method comprising cleaning the road surface, liquifying an electrically conductive material (15) by means of a metal spraying device and applying the conductive material directly to the previously roughened road surface (11) in a film-like manner, resulting in the conductor layer (15), sealing the conductor layer with a protective covering (14) consisting of a fast-setting plastics material which is resistant to temperature, abrasion and aggressive substances and remains elastic within certain limits.

2. Method according to claim 1, comprising initially bridging any joints (18) in the road surface (11) by means of connecting pieces (19) which are elastic within certain limits, then applying the conductor layer (15) and attaching the protective covering (14).

3. Method for applying an inductive conductor layer on a road surface, the conductor layer being enclosed by a protective covering, the method comprising applying a carrier layer (13) on the road surface, roughening the surface of the carrier layer, the carrier layer being composed of a fast-setting plastics material which is resistant to temperature, abrasion and aggressive substances and remains elastic within certain limits, liquifying an electrically conductive material (15) by means of a metal spraying device and applying the conductive material to the carrier layer (13) to form the conductor layer (15), sealing the conductor layer with a protective covering (14) which consists of the same plastics material as the carrier layer (13).

* * * * *

UNITED STATES PATENT AND TRADEMARK OFFICE
CERTIFICATE OF CORRECTION

PATENT NO. : 4,941,770

DATED : July 17, 1990

INVENTOR(S) : Hans-Jürgen Gemmer

It is certified that error appears in the above-identified patent and that said Letters Patent is hereby corrected as shown below:

On the title page, item [76] should read:
--[76] Inventor: Hans-Jürgen Gemmer, Angelstr. 14, D-6251 Heistenbach, Federal Republic of Germany--.

Signed and Sealed this

Nineteenth Day of February, 1991

Attest:

HARRY F. MANBECK, JR.

*Attesting Officer* — *Commissioner of Patents and Trademarks*